US006528523B2

(12) United States Patent
Njoroge et al.

(10) Patent No.: US 6,528,523 B2
(45) Date of Patent: Mar. 4, 2003

(54) FARNESYL PROTEIN TRANSFERASE INHIBITORS

(75) Inventors: F. George Njoroge, Warren, NJ (US); Bancha Vibulbhan, Kenilworth, NJ (US); Viyyoor M. Girijavallabhan, Parsippany, NJ (US); Xiongwei Shi, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/995,156

(22) Filed: Nov. 27, 2001

(65) Prior Publication Data

US 2002/0115679 A1 Aug. 22, 2002

Related U.S. Application Data

(60) Provisional application No. 60/253,971, filed on Nov. 29, 2000.

(51) Int. Cl.[7] .................. A61K 31/4545; C07D 401/14; C07D 401/04; A61P 35/00
(52) U.S. Cl. .......................................... 514/290; 546/93
(58) Field of Search ............................. 514/290; 546/93

(56) References Cited

U.S. PATENT DOCUMENTS

| 5,661,152 | A | * | 8/1997 | Bishop ................ 514/254 |
| 5,684,013 | A | | 11/1997 | Afonso et al. |
| 5,696,121 | A | | 12/1997 | Bishop et al. ............ 514/254 |
| 5,700,806 | A | | 12/1997 | Doll et al.. |
| 5,703,090 | A | | 12/1997 | Afonso et al. |
| 5,719,148 | A | * | 2/1998 | Bishop ................ 514/228.2 |
| 5,784,442 | A | | 7/1998 | Doll et al. ................. 514/290 |
| 5,801,175 | A | | 9/1998 | Afonso et al. |
| 5,807,852 | A | | 9/1998 | Doll et al. |
| 5,852,034 | A | | 12/1998 | Njoroge et al. |
| 5,861,395 | A | | 1/1999 | Taveras et al. |
| 5,874,442 | A | * | 2/1999 | Doll ...................... 514/290 |
| 5,925,639 | A | | 7/1999 | Doll et al. |
| 5,925,757 | A | * | 7/1999 | Mallams .................. 544/361 |
| 5,939,416 | A | | 8/1999 | Rane et al. |
| 5,945,429 | A | | 8/1999 | Taveras et al. |
| 5,958,939 | A | | 9/1999 | Afonso et al. |
| 5,985,879 | A | | 11/1999 | Taveras et al. |
| 6,030,982 | A | | 2/2000 | Njoroge et al. |
| 6,039,683 | A | | 3/2000 | Njoroge et al. |
| 6,040,305 | A | | 3/2000 | Taveras et al. |
| 6,051,582 | A | | 4/2000 | Taveras et al. |
| 6,071,907 | A | | 6/2000 | Njoroge et al. .......... 514/228.2 |
| 6,096,757 | A | | 8/2000 | Bishop et al. |
| 6,124,295 | A | | 9/2000 | Taveras et al. |
| 6,143,758 | A | | 11/2000 | Doll et al. ................. 514/290 |
| 6,159,984 | A | | 12/2000 | Guzi et al. |
| 6,214,827 | B1 | | 4/2001 | Afonso et al. |
| 6,214,828 | B1 | | 4/2001 | Doll et al. .............. 514/253.03 |
| 6,221,322 | B1 | | 4/2001 | Inamura et al. |
| 6,228,856 | B1 | | 5/2001 | Njoroge et al. |
| 6,228,865 | B1 | | 5/2001 | Doll et al. |
| 6,239,140 | B1 | | 5/2001 | Cooper et al. |
| 6,242,458 | B1 | | 6/2001 | Bishop et al. ............... 514/290 |
| 6,333,333 | B1 | | 12/2001 | Bishop et al. |
| 6,358,968 | B1 | | 3/2002 | Remiszewski et al. |
| 6,362,188 | B1 | | 3/2002 | Guzi et al. |
| 6,365,588 | B1 | | 4/2002 | Bishop et al. ............ 514/228.2 |
| 6,372,747 | B1 | | 4/2002 | Taveras et al. |
| 6,410,451 | B2 | | 6/2002 | Remiszewski et al. . 514/253.03 |
| 6,410,541 | B2 | | 6/2002 | Remiszewski et al. |
| 6,432,959 | B1 | | 8/2002 | Cooper et al. |

OTHER PUBLICATIONS

Claims of Co–pending Application 09/520,449 filed Mar. 8, 2000.
Claims of Co–pending Application 09/940,811 filed Aug. 28, 2001.
Claims of Co–pending Application 09/215,603 filed Dec. 17, 1998.
Claims of Co–pending Application 09/094,687 filed Jun. 15, 1998.

* cited by examiner

*Primary Examiner*—Evelyn Mei Huang
(74) *Attorney, Agent, or Firm*—Robert L. Bernstein; Henry C. Jeanette

(57) ABSTRACT

The present invention describes compounds useful for the inhibition of Farnesyl Protein Transferase. This invention also discloses pharmaceutical compositions comprising such compounds as well as methods of using them to treat disorders associated with FPT.

7 Claims, No Drawings

FARNESYL PROTEIN TRANSFERASE INHIBITORS

REFERENCE TO RELATED APPLICATIONS

This application claims the benefit of U.S. Provisional Application Ser. No. 60/253,971 filed Nov. 29, 2000.

BACKGROUND

WO 95/10514, WO 95/10515, WO 95/10516, published Apr. 20, 1995, WO 97/23478, published Jul. 3, 1997, and WO 98/57949, published Dec. 32, 1998, disclose tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds selected from the group consisting of:

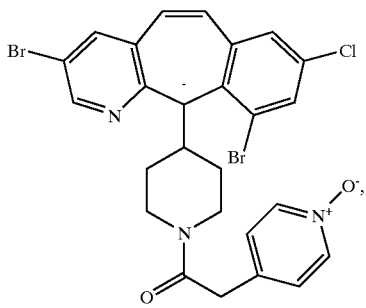

I

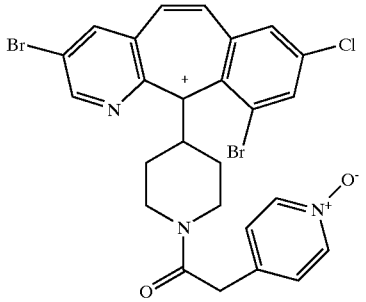

II

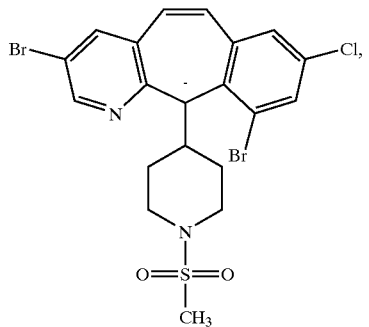

III

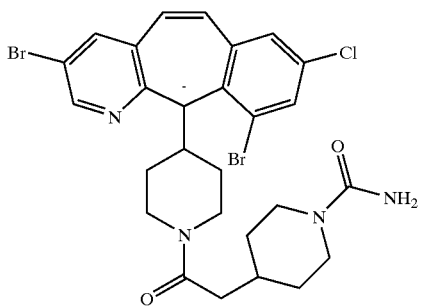

IV

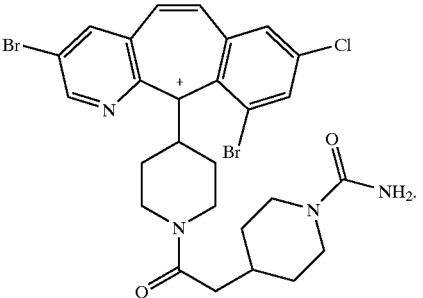

V and

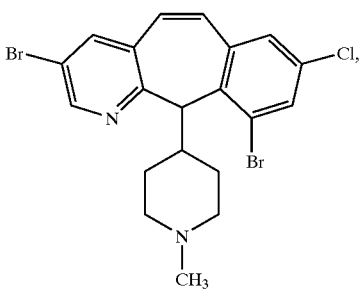

VI

In another embodiment, this invention provides a process for producing intermediate compound (4)

4 comprising:

(a) dissolving compound (3)

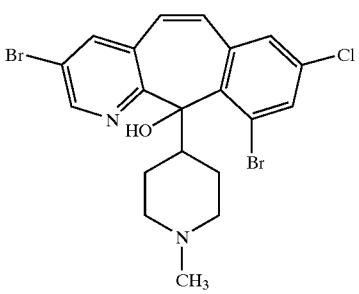

in a solvent mixture comprising a suitable aprotic solvent (such as, for example, $CH_2Cl_2$, $CHCl_3$ or benzene) and dimethylacetamide, said aprotic solvent to dimethylacetamide in a molar ratio in a range of about 1–10:1.0. Preferably said aprotic solvent to dimethylacetamide is in a molar ratio of 3.5:1.0;

(b) cooling the reaction mixture to a temperature of between about (−)10° C. and about (+)10° C.;

(c) adding about 10 to about 40 molar equivalents of thionyl bromide (i.e., $SOBr_2$; Preferably the $SOBr_2$ is freshly prepared (i.e., prepared and used within 72 hours) Still more preferably, the SOBr2 is prepared and used within 48 hours.

(d) stirring the reaction mixture at a temperature between about (−)10° C. and about (+)40° C., (in general the reaction is stirred for about 4 to about 10 hours, preferably about 4 hours);

(e) basifying the reaction mixture with an appropriate aqueous alkaline solution such as, a solution of NaOH, $NaHCO_3$, $NH_4OH$, and the like. Preferably the aqueous alkaline solution concentration is 1N; and (f) extracting the resulting solution with a suitable organic solvent such as, for example, $CH_2Cl_2$, ethyl acetate, and the like.

In general, intermediate compound (4) obtained from the above process, is purified using techniques well known in the art, (e.g., flash silica gel column chromatography, HPLC, and the like).

The compounds of this invention are potent Farnesyl Protein Transferase inhibitors having good pharmacokinetic stability.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount (e.g. a therapeutically effective amount) of the tricyclic compounds listed below. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount (e.g. a therapeutically effective amount) of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount (e.g., a therapeutically effective amount) of the tricyclic compounds, described herein, to a mammal (e.g., a human) in need of such treatment. In particular, this invention provides a method for inhibiting or treating the growth of tumors expressing an activated Ras oncogene by the administration of an effective amount (e.g. a therapeutically effective amount) of the below described compounds.

Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, melanoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount (e.g. a therapeutically effective amount) of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as Ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION

As used herein, the following terms are used as defined below unless otherwise indicated:

MH+-represents the molecular ion plus hydrogen of the molecule in the mass spectrum;
BOC-represents tert-butyloxycarbonyl;
CH$_2$Cl$_2$-represents dichloromethane;
CIMS-represents chemical ionization mass spectrum;
DEC-represents EDCl which represents 1-(3-dimethylaminopropyl)-3-ethylcarbodiimide hydrochloride;
DMF-represents N,N-dimethylformamide;
Et-represents ethyl;
EtOAc-represents ethyl acetate;
EtOH-represents ethanol;
HOBT-represents 1-hydroxybenzotriazole hydrate;
IPA-represents isopropanol;
iPrOH-represents isopropanol;
Me-represents methyl;
MeOH-represents methanol;
MS-represents mass spectroscopy;
FAB-represents FABMS which represents fast atom bombardment mass spectroscopy;
HRMS-represents high resolution mass spectroscopy;
NMM-represents N-methylmorpholine;
Et$_3$N-represents TEA which represents triethylamine;
t-BUTYL-represents —C—(CH$_3$)$_3$;
THF-represents tetrahydrofuran;
FPT-represents Farnesyl Protein Transferase;

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The compounds of this invention can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

The following processes may be employed to produce compounds of the invention.

EXAMPLES

Preparative Example 1

Step 1

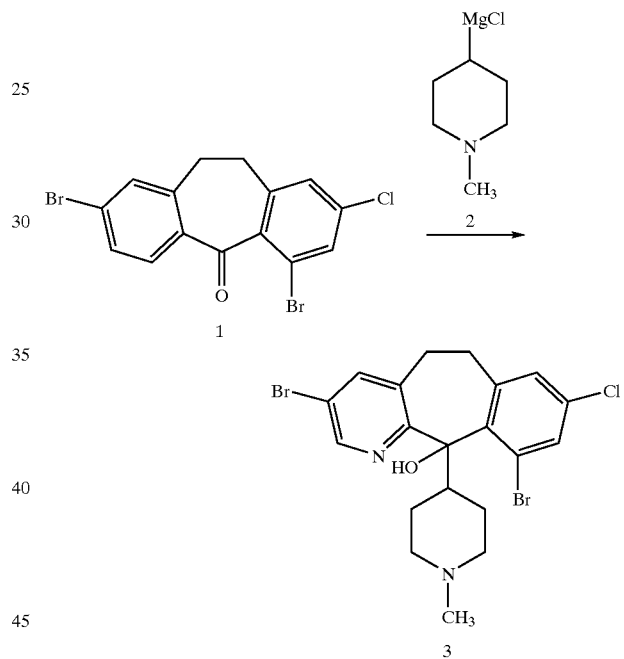

Compound (1) (see Preparative Example 9 Step D of US Patent Case No. IN0549), 20 g (0.05 mol) was dissolved in 1 L of dry THF. This solution was added to a solution of Grignard reagent (80 mL, 1.56M in THF (250 mL), 0.125 mol, 2.5 equiv.) cooled to −40° C. The reaction mixture was agitated for 0.5 h and then quenched with NH$_4$Cl (100 mL). THF was removed by distillation (1200 mL) and 500 mL of CH$_2$Cl$_2$ were added and the pH adjusted to 5 with 10% HCl. The aqueous phase was extracted with CH$_2$Cl$_2$ (250 mL) and the organic phase was separated from the aqueous phase. Combined organic phases were washed with sat. NaHCO$_3$ and then dried over anhydrous Na$_2$SO$_4$ and passed through a short pad of celite. Acetonitrile 300 mL was then added and CH$_2$Cl$_2$ was distilled until only 300 mL remained. Crytstals precipitated out and were collected and dried to give 15.9 g (64%) of the target azaketone; MH+=501.

Step 2

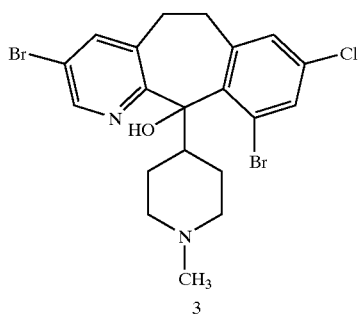
3

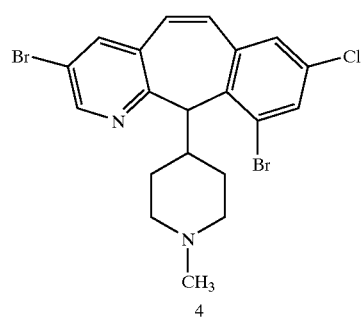
4

To a solution of compound (3) (5.0 g, 9.97 mmol) from Step 1 above, in CH$_2$Cl$_2$ (25 mL) was added dimethylacetamide (9.5 g, 109 mmol, 10 mL) and the reaction mixture was brought to 0° C. Thionyl bromide (35 mL freshly prepared from NaBr and SOCl$_2$) was slowly added to the reaction mixture. The reaction was stirred for 4 h. The reaction mixture was then partitioned between saturated NaHCO$_3$ and CH$_2$Cl$_2$. The organic phase was dried with Na$_2$SO$_4$ and then purified by flash column chromatography (silica gel, 1% MeOH—NH$_3$—CH$_2$Cl$_2$) to give the product as a solid (0.82 g, 17% yield); mp=73–75; MS (FAB) m/z 483 (MH$^+$).

Step 3

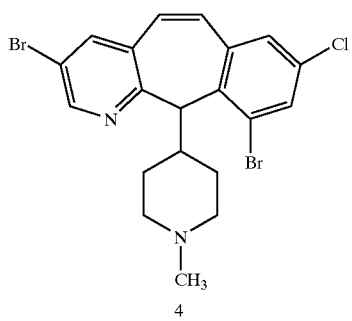
4

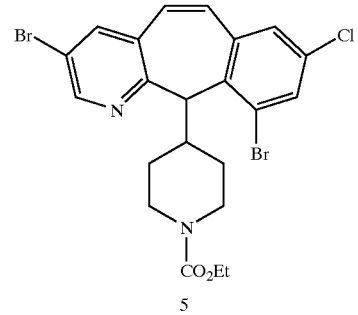
5

To a solution of compound (4) (3.51 g, 7.3 mmol) from Step 2 above, in toluene (70 mL) was slowly added Et$_3$N (2.5 g, 25 mmol, 3.6 mL) and the reaction mixture was brought to reflux. Ethyl chloroformate (3.96 g, 36.5 mmol, 3.5 mL) was added to the reaction mixture and refluxing continued for 16 h. The reaction mixture was partitioned between EtOAc and 1N NaOH. The organic phase was dried with MgSO$_4$ and then purified by flash column chromatography (silica gel, 20% EtOAc-hexane) to give the product as a solid (3.70 g, 94% yield); mp=63–64; MS (FAB) m/z 541 (MH$^+$).

Step 4

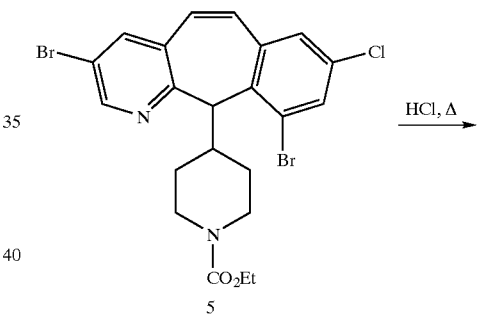
5

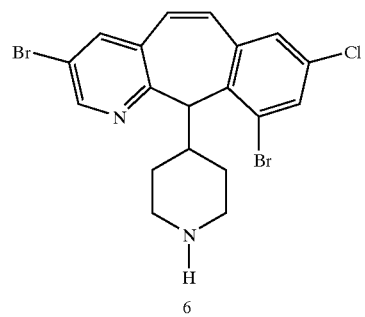
6

To 80 mL of Conc. HCl was added Compound (5) (3.65 g, 6.8 mmol) from Step 3 above. The reaction mixture was refluxed for 16 h. It was then cooled, poured into ice and basified to pH=10 with aqueous 50% NaOH. The aqueous phase was extracted with CH$_2$Cl$_2$. Concentration of the organic phase afforded 2.02 g of Compound (6) mp=88–89° C.; MS m/z (rel intens) 469 (MH$^+$).

Step 5

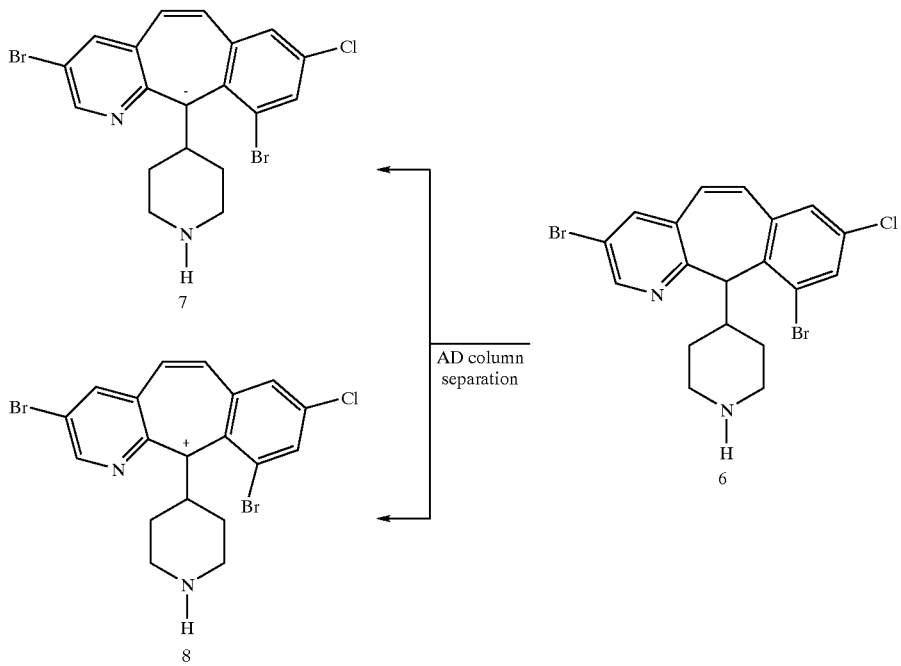

Separation on HPLC using a Chiralpack AD column and 20% isopropanol-80% hexane-0.2% diethylamine as eluent gave enantiomeric amines 7 and 8.

Compound (7): mp=82–83; $[\alpha]_D^{22}$=−116.8° (7.64 mg/2 mL CHCl$_3$); MS (FAB) m/z 469 (MH$^+$).

Compound (8): mp=88–89; $[\alpha]_D^{22}$=+150.0° (6.02 mg/2 mL CHCl$_3$); MS (FAB) m/z 469 (MH$^+$).

Preparative Example 2
Step 1

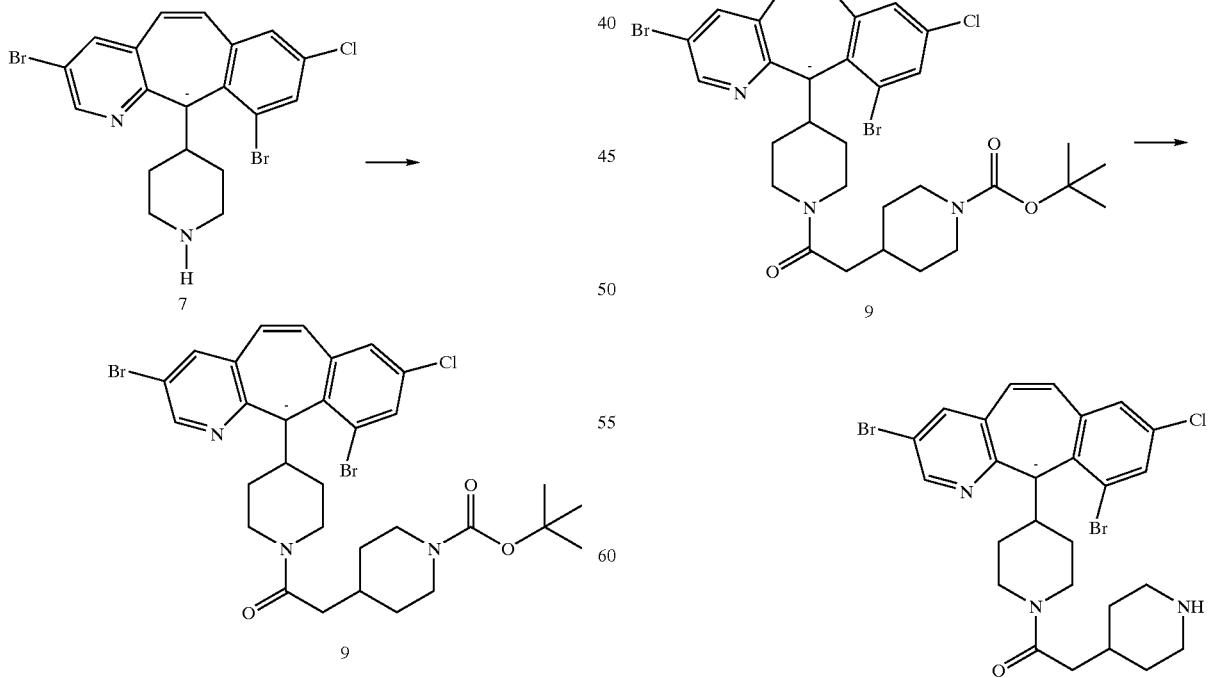

A mixture of Compound (7) (0.74 g, 1.58 mmol) from Preparative Example 1, Step 5, piperidylacetic acid N-BOC (0.72 g, 3.16 mmol), HOBT (0.27 g, 2.05 mmol), DEC (0.39 g, 2.05 mmol) and dry DMF (10 mL) was stirred at 25° C. for 16 hrs. The mixture was concentrated in vacuo, diluted with CH$_2$Cl$_2$ and washed with saturated NaHCO$_3$ (aqueous) and 10% NaH$_2$PO$_4$ (aqueous). The organic phase was dried over anhydrous MgSO$_4$ and concentrated in vacuo to provide to give the (−) isomer, Compound (9) as a solid (1.19 g, 100% yield); mp=73–74; MS (FAB) m/z 694.2 (MH$^+$).

Step 2

A solution of Compound (9) (1.06 g, crude residue from Step 1 above), anhydrous dichloromethane (15 mL) and trifluoroacetic acid (4 mL) was stirred at 0° C. for 3 h. The solution was cooled in ice-water and treated slowly with 50% aqueous sodium hydroxide until basic. The mixture was poured into dichloromethane and washed with water. The organic phase was dried over anhydrous MgSO$_4$ and concentrated in vacuo to give Compound (10) (0.82 g, 100% yield); mp=94–95° C.; MS (FAB) m/z 594 (MH$^+$).

Example 1

Preparation of Compound (11)

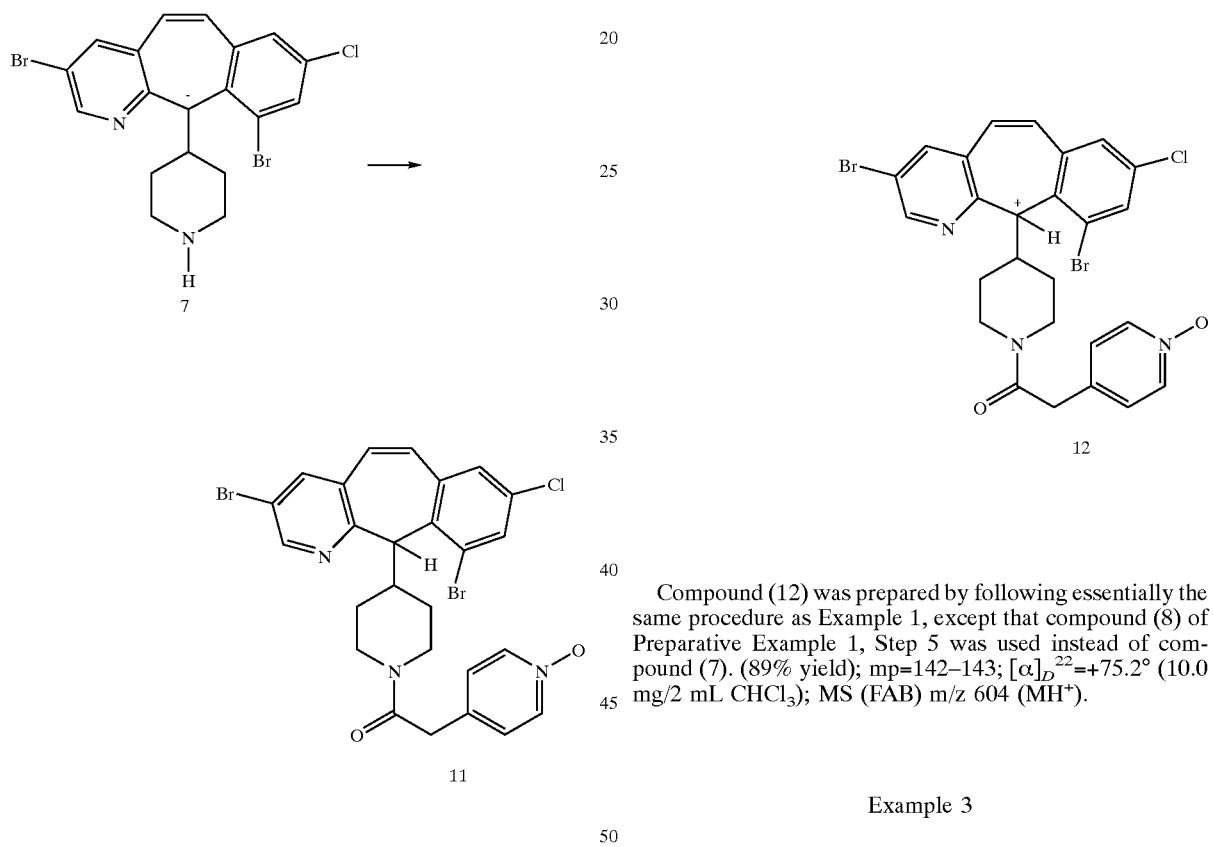

A mixture of Compound (7) (0.2 g, 0.43 mmol) (from Preparative Example 1 Step 5), pyridylacetic acid N-oxide (0.13 g, 0.86 mmol), HOBT (0.075 g, 0.55 mmol), DEC (0.106 g, 0.55 mmol), N-methylmorpholine (0.06 mL, 0.55 mmol) and dry DMF (5 mL) was stirred at 25° C. for 16 hrs. The mixture was concentrated in vacuo, diluted with CH$_2$Cl$_2$ and washed with Sat. NaHCO$_3$ (aqueous) and saturated NaH$_2$PO$_4$ (aqueous). The organic phase was dried over anhydrous MgSO$_4$ and concentrated in vacuo to provide a residue which was purified by flash column chromatography (silica gel, 5% MeOH/CH$_2$Cl$_2$+NH$_4$OH) to give Compound (11) as a solid (0.12 g, 73% yield). mp=137–139; $[\alpha]_D^{22}$=–70.1° (10.1 mg/2 mL CHCl$_3$); MS (FAB) m/z 604 (MH$^{30}$).

Example 2

Preparation of Compound 12

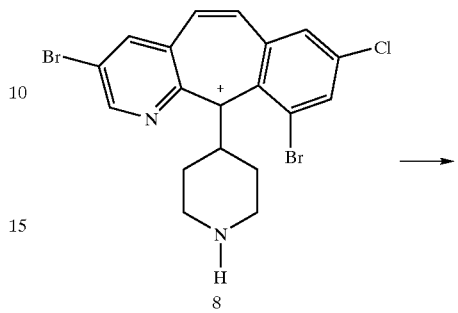

Compound (12) was prepared by following essentially the same procedure as Example 1, except that compound (8) of Preparative Example 1, Step 5 was used instead of compound (7). (89% yield); mp=142–143; $[\alpha]_D^{22}$=+75.2° (10.0 mg/2 mL CHCl$_3$); MS (FAB) m/z 604 (MH$^+$).

Example 3

Preparation of Compound 13

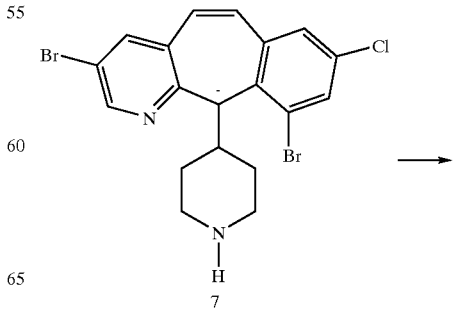

-continued

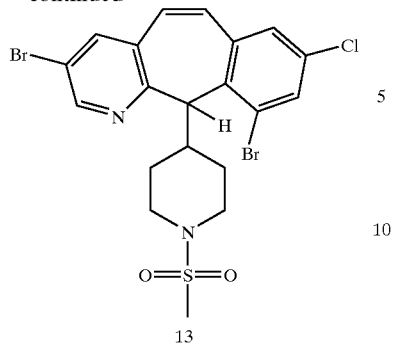

13

To Compound (7) (0.10 g, 0.21 mmol) from Preparative Example 1, Step 5, and triethylamine (0.043 g, 0.06 mL, 0.43 mmol) dissolved in anhydrous dichloromethane (5 mL) was added methanesulfonyl chloride (0.037 g, 0.03 mL, 0.32 mmol). After stirring at room temperature overnight, the solution was diluted with dichloromethane (100 mL), washed with saturated NaHCO$_3$ and dried over anhydrous magnesium sulfate. Filtration and concentration in vacuo afforded Compound (13) (0.10 g, 89%, mp=84–85° C.); $[\alpha]_D^{22}$=−73.1° (7 mg/2 mL CHCl$_3$); MS (FAB) m/z 547 (MH$^+$).

Example 4

Preparation of Compound (14)

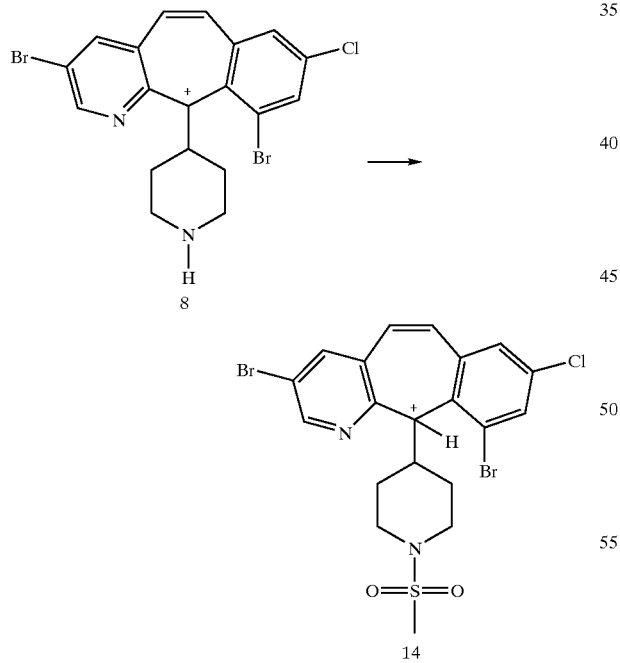

Compound (14) was prepared by following essentially the same procedure as Example 3, except that compound (8) of Preparative Example 1, Step 5 was used instead of compound (7); (99% yield); mp=91–92; $[\alpha]_D^{22}$=+95.0° (10.0 mg/2 mL CHCl$_3$); MS (FAB) m/z 547 (MH$^+$).

Example 5

Preparation of Compound (15)

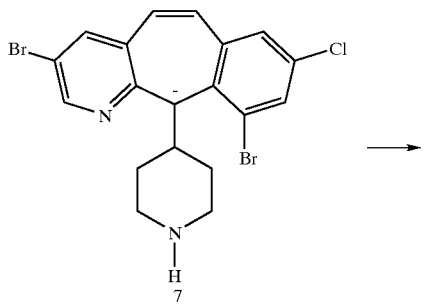

To a solution of Compound (7) of Preparative Example 1 step 5 (0.78 g, 1.31 mmol) in anhydrous dichloromethane (20 mL) was added trimethylsilylisocyanate (1.21 g, 1.42 mL, 10.51 mmol). After stirring at 25° C. for 48 h the solution was poured into dichloromethane and washed with saturated aqueous sodium bicarbonate and brine. The organic phase was dried over anhydrous MgSO$_4$ and concentrated in vacuo to give an off-white solid. Further purification by flash column chromatography (silica gel) using 5% methanol-dichloromethane with ammonium hydroxide afforded Compound (15) as a white solid (0.56 g, 67% yield). Recrystallization from acetone provided an analytical sample; mp=146–147° C.; $[\alpha]_D^{25}$=−68.8° (8.2 mg/2 mL, CHCl$_3$); MS (FAB) m/z 637 (MH$^+$).

Example 6

Preparation of Compound (16)

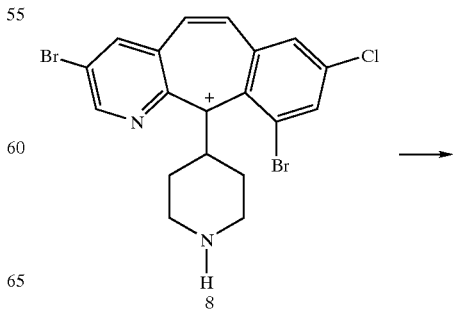

-continued

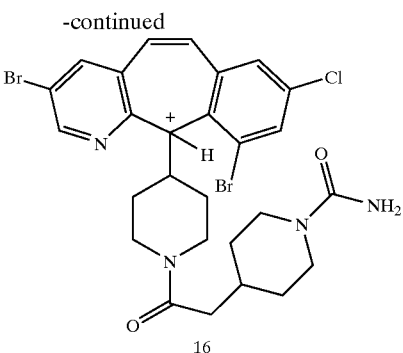

16

Compound (16) was prepared by following essentially the same procedure as Example 5, except that compound (8) of Preparative Example 1, Step 5 was used instead of compound (7). (74% yield); mp=142–143; $[\alpha]_D^{22}$=+78.3° (11.8 mg/2 mL CHCl$_3$); MS (FAB) m/z 637 (MH$^+$).

ASSAYS

1. In Vitro Enzyme Assay:

Inhibition of farnesyl protein transferase. Farnesyl protein transferase (FPT) was partially purified from rat brain by ammonium sulfate fractionation followed by Q-Sepharose (Pharmacia, Inc.) anion exchange chromatography essentially as described by Yokoyama et al (Yokoyama, K., et al., (1991). Implications for protein prenylation specificity, Proc. Natl. Acad. Sci USA 88: 5302–5306, the disclosure of which is incorporated herein by reference thereto). Human farnesyl protein transferase was also expressed in *E. coli*, using cDNA clones encoding both the a and b subunits. The methods used were similar to those published (Omer, C. et al., (1993), Characterization of recombinant human farnesyl protein transferase: Cloning, expression, farnesyl diphosphate binding, and functional homology with yeast prenyl-protein transferases, Biochemistry 32:5167–5176). Human farnesyl protein transferase was partially-purified from the soluble protein fraction of *E. coli* as described above. The tricyclic farnesyl protein transferase inhibitors disclosed herein inhibited both human and rat enzyme with similar potencies. Two forms of val$^{12}$-Ha-Ras protein were prepared as substrates for these enzymes, differing in their carboxy terminal sequence. One form terminated in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins were constructed so that the proteins contain an amino-terminal extension of 6 histidine residues. Both proteins were expressed in *Escherichia coli* and purified using metal chelate affinity chromatography. The radio labelled isoprenyl pyrophosphate substrates, [$^3$H]farnesyl pyrophosphate and [$^3$H] geranylgeranyl pyrophosphate, were purchased from DuPont/New England Nuclear.

Several methods for measuring farnesyl protein transferase activity have been described (Reiss et al 1990, Cell 62: 81; Schaber et al 1990, J. Biol. Chem. 265: 14701; Manne et al 1990, PNAS 87: 7541; and Barbacid & Manne 1993, U.S. Pat. No. 5,185,248). The activity was assayed by measuring the transfer of [$^3$H]farnesyl from [$^3$H]farnesyl pyrophosphate to Ras-CVLS using conditions similar to those described by Reiss et al. 1990 (Cell 62: 81) The reaction mixture contained 40 mM Hepes, pH 7.5; 20 mM magnesium chloride; 5 mM dithiothreitol; 0.25 $\mu$M [$^3$H] farnesyl pyrophosphate; 10 ml Q-Sepharose-purified farnesyl protein transferase; the indicated concentration of tricyclic compound or dimethylsulfoxide (DMSO) vehicle control (5% DMSO final); and 5 mM Ras-CVLS in a total volume of 100 ml. The reaction was allowed to proceed for 30 minutes at room temperature and then stopped with 0.5 ml of 4% sodium dodecyl sulfate (SDS) followed by 0.5 ml of cold 30% TCA. Samples were allowed to sit on ice for 45 minutes and precipitated Ras protein was then collected on GF/C filter paper mats using a Brandel cell harvester. Filter mats were washed once with 6% TCA, 2% SDS and radioactivity was measured in a Wallac 1204 Betaplate BS liquid scintillation counter. Percent inhibition was calculated relative to the DMSO vehicle control.

2. Soft Agar Assay:

Anchorage-independent growth is a characteristic of tumorigenic cell lines. Human tumor cells are suspended in growth medium containing 0.3% agarose and an indicated concentration of a farnesyl transferase inhibitor. The solution is overlayed onto growth medium solidified with 0.6% agarose containing the same concentration of farnesyl transferase inhibitor as the top layer. After the top layer is solidified, plates are incubated for 10–16 days at 37° C. under 5% CO$_2$ to allow colony outgrowth. After incubation, the colonies are stained by overlaying the agar with a solution of MTT (3-[4,5-dimethylthiazol-2-yl]-2,5-diphenyltetrazolium bromide, Thiazolyl blue) (1 mg/mL in PBS). Colonies are counted and the IC$_{50}$'s determined.

Results of the assay are shown in Table 1 below:

TABLE 1

| R= | Enantiomer | FPT IC50 (nM) | Soft agar IC50 ($\mu$M) |
|---|---|---|---|
| (structure) | (−) | 0.32 | 0.03 |
| (structure) | (+) | >17 | NA |

TABLE 1-continued

[Structure: tricyclic compound with Br, Cl, Br substituents and N-R piperidine]

| R= | Enantiomer | FPT IC50 (nM) | Soft agar IC50 (μM) |
|---|---|---|---|
| —S(O)₂—CH₃ | (−) | 3.3 | >0.50 |
| —S(O)₂—CH₃ | (+) | >18 | NA |
| —C(O)CH₂-[4-piperidinyl-N-C(O)NH₂] | (−) | 0.40 | 0.05 |
| —C(O)CH₂-[4-piperidinyl-N-C(O)NH₂] | (+) | 16 | NA |

ADMINISTRATION AND DOSAGE

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations, which are intended to be converted, shortly before use, to liquid form preparations for either oral or parenteral administration. Such liquid forms include solutions, suspensions and emulsions.

The compounds of the invention are preferably administered orally, once a day.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

The compounds of this invention are administered to a patient in need of such treatment (e.g. a mammal, such as a human being) in an effective amount, e.g. a therapeutically effective amount. The amount administered is enough to inhibit FPT.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound selected from the group consisting of

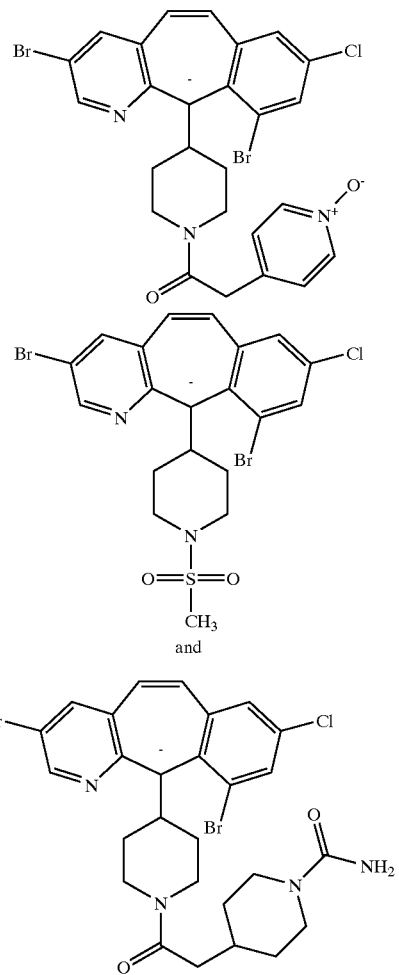

and

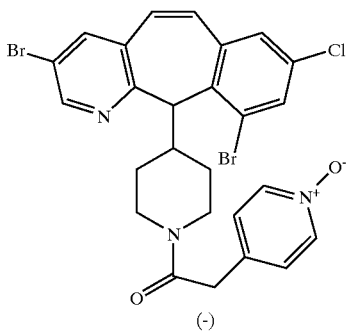

or a pharmaceutically acceptable salt thereof.

2. A compound of the formula

3. A compound of the formula

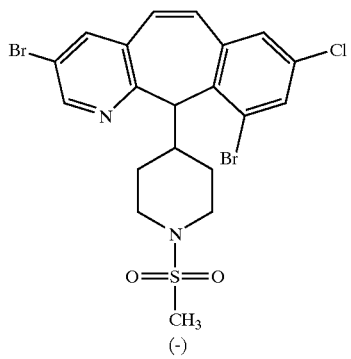

or a pharmaceutically acceptable salt thereof.

4. A compound of the formula

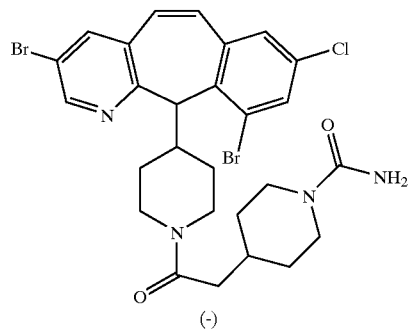

or a pharmaceutically acceptable salt thereof.

5. A method of inhibiting FPT comprising administering to a patient in need of such treatment a compound of claim 1 in an amount effective for inhibiting FPT.

6. A pharmaceutical composition comprising a compound of claim 1 in combination with a pharmaceutically acceptable carrier.

7. A method of inhibiting the growth of pancreatic tumor cells, lung tumor cells, myeloid leukemia tumor cells, thyroid follicular tumor cells, myelodysplastic tumor cells, epidermal carcinoma tumor cells, bladder tumor cells or colon tumor cells, in a patient in need of such treatment by inhibition of farnesyl protein transferase, comprising, administering to said patient, an effective tumor inhibiting amount of a compound of claim 1.

* * * * *